(12) United States Patent
Spector

(10) Patent No.: US 10,709,883 B2
(45) Date of Patent: Jul. 14, 2020

(54) BANDAGE WITH MICRONEEDLES FOR ANTIMICROBIAL DELIVERY AND FLUID ABSORPTION FROM A WOUND

(71) Applicant: Donald Spector, New York, NY (US)

(72) Inventor: Donald Spector, New York, NY (US)

(*) Notice: Subject to any disclaimer, the term of this patent is extended or adjusted under 35 U.S.C. 154(b) by 380 days.

(21) Appl. No.: 15/873,162

(22) Filed: Jan. 17, 2018

(65) Prior Publication Data

US 2018/0140817 A1 May 24, 2018

Related U.S. Application Data

(63) Continuation-in-part of application No. 14/693,049, filed on Apr. 22, 2015, now abandoned, which is a continuation-in-part of application No. 13/795,055, filed on Mar. 12, 2013, now abandoned, which is a continuation-in-part of application No. 12/752,568, filed on Apr. 1, 2010, now Pat. No. 8,419,668.

(60) Provisional application No. 62/573,042, filed on Oct. 16, 2017, provisional application No. 62/128,474, filed on Mar. 4, 2015, provisional application No. 61/310,332, filed on Mar. 4, 2010.

(51) Int. Cl.
| | |
|---|---|
| *A61F 13/84* | (2006.01) |
| *A61F 5/40* | (2006.01) |
| *A61M 37/00* | (2006.01) |
| *A61F 13/02* | (2006.01) |
| *A61F 13/00* | (2006.01) |
| *A61L 15/44* | (2006.01) |

(52) U.S. Cl.
CPC ... *A61M 37/0015* (2013.01); *A61F 13/00063* (2013.01); *A61F 13/0206* (2013.01); *A61L 15/44* (2013.01); *A61L 2300/404* (2013.01); *A61L 2300/62* (2013.01); *A61M 2037/003* (2013.01); *A61M 2037/0023* (2013.01); *A61M 2205/0205* (2013.01); *A61M 2205/502* (2013.01); *A61M 2205/8206* (2013.01)

(58) Field of Classification Search
CPC ...... A61M 37/0015; A61M 2037/0023; A61M 2205/0205; A61M 2205/502; A61M 2205/8206; A61M 2037/003; A61L 15/44; A61L 2300/404; A61L 2300/62; A61F 13/00063; A61F 13/0206
See application file for complete search history.

(56) References Cited

U.S. PATENT DOCUMENTS

| | | |
|---|---|---|
| 3,504,064 A | 3/1970 | Bauer |
| 4,131,114 A | 12/1978 | Kirkpatrick et al. |
| 4,241,007 A | 12/1980 | Tanaka et al. |

(Continued)

*Primary Examiner* — Anna K Kinsaul
*Assistant Examiner* — Camtu T Nguyen
(74) *Attorney, Agent, or Firm* — Collard & Roe, P.C.

(57) ABSTRACT

A bandage is formed of a film layer, an adhesive applied to the film layer, and an absorbent layer connected to the film layer. The absorbent layer comprises a compressed fabric. A plurality of microneedles are disposed within the absorbent layer, each microneedle having an end that extends through the absorbent layer and is configured to penetrate a wound when the bandage is applied over the wound. An antimicrobial agent disposed within the bandage and in communication some of the microneedles, so that upon application of the bandage to the wound, the antimicrobial agent is transported though said microneedles to the wound. The microneedles not in communication with the microbial agent are configured to transport fluid from the wound to the absorbent layer.

12 Claims, 3 Drawing Sheets

(56) References Cited

U.S. PATENT DOCUMENTS

| | | |
|---|---|---|
| 4,273,115 A | 6/1981 | Holland et al. |
| 4,376,438 A | 3/1983 | Straube et al. |
| 4,411,262 A | 10/1983 | Von Bonin et al. |
| 4,433,680 A | 2/1984 | Yoon |
| 4,454,873 A | 6/1984 | Laufenberg et al. |
| 4,502,479 A | 3/1985 | Garwood et al. |
| 4,411,262 B1 | 7/1985 | Von Bonin et al. |
| 4,841,958 A | 6/1989 | Ersfeld et al. |
| 4,984,566 A | 1/1991 | Sekine et al. |
| 5,005,566 A | 4/1991 | Klintworth, Jr. |
| 5,172,629 A | 12/1992 | Merry |
| 5,277,954 A | 1/1994 | Carpenter et al. |
| 5,370,927 A | 12/1994 | Scholz et al. |
| 5,449,550 A | 9/1995 | Yasis et al. |
| 5,474,522 A | 12/1995 | Scholz et al. |
| 5,807,292 A | 9/1998 | Delmore |
| 5,823,983 A | 10/1998 | Rosofsky et al. |
| 5,997,492 A | 12/1999 | Delmore et al. |
| 6,063,980 A | 5/2000 | Peterson et al. |
| 6,077,240 A | 6/2000 | Sholz et al. |
| 6,967,261 B1 | 11/2005 | Soerens et al. |
| 8,026,407 B2 | 9/2011 | Downs et al. |
| 8,333,743 B2 | 12/2012 | Toreki et al. |
| 2007/0073201 A1 | 3/2007 | Campagna et al. |
| 2011/0092871 A1 | 4/2011 | Fabo et al. |
| 2011/0311610 A1 | 12/2011 | Mathies |
| 2014/0048436 A1 | 2/2014 | Spector |

BANDAGE WITH MICRONEEDLES FOR ANTIMICROBIAL DELIVERY AND FLUID ABSORPTION FROM A WOUND

CROSS-REFERENCE TO RELATED APPLICATIONS

This application is claims priority from U.S. Provisional Application No. 62/573,042 filed on Oct. 16, 2017. This application is also a continuation in part of U.S. patent application Ser. No. 14/693,049, which claims priority under 35 USC 119(e) of U.S. Provisional Application Ser. No. 62/128,474, filed on Mar. 4, 2015 and which application is also a continuation-in-part of U.S. patent application Ser. No. 13/795,055, filed on Mar. 12, 2013, which is a continuation-in-part of U.S. patent application Ser. No. 12/752,568, filed on Apr. 1, 2010 (now U.S. Pat. No. 8,419,668 issued Apr. 16, 2013), which claims priority under 35 USC 119(e) of U.S. Provisional Application Ser. No. 61/310,332, filed on Mar. 4, 2010. The disclosures of all of these prior applications are herein incorporated by reference.

BACKGROUND OF THE INVENTION

1. Field of the Invention

The present invention relates to a bandage having a layer of absorbent material. In particular, the invention relates to a bandage having a layer of containing a plurality of microneedles that are adapted to suction fluid from a wound and also to inject antimicrobial agents in to the wound.

2. The Prior Art

Present bandage strips typically consist of a layer of gauze padding connected to a longer strip of adhesive film or fabric. The gauze padding typically has a non-stick layer on its side facing the wound to keep the gauze from sticking to the wound. In addition, some bandages are treated with antimicrobial agents to prevent infection of the wound. For example, U.S. Pat. No. 6,967,261 to Soerens et al. discloses a bandage having a multilayer system connected to an adhesive strip. An antimicrobial agent is supplied to the bandage such that the agent can contact the wound.

While this type of bandage may be useful, some wounds are deep and/or large enough that the antimicrobial agent is insufficient for treating the entire wound. The bodily fluids collect in the wound and can cause infection.

SUMMARY OF THE INVENTION

It is therefore an object of the invention to provide a bandage having an antimicrobial agent and which also draws fluid away from the wound to speed healing and allow the agent to reach all areas of the wound.

This object is accomplished by a bandage comprising a film layer having a top surface and a bottom surface, an adhesive applied to the bottom surface, and an absorbent layer connected to the bottom surface. The absorbent layer comprises an absorbent material that is also equipped with a plurality of microneedles that either absorb fluid from the wound, or are filled with antimicrobial agent, which is released into the wound. The needles act as conduits both into and out of the wound, so that over time, fluid collecting in the wound area is continually suctioned away and treated, thus decreasing healing time and risk of infection. The needles that absorb the fluid from the wound are attached directly to the absorbent material, and capillary action forces the fluid from the wound up the needles, where it is absorbed by the absorbent layer. At the same time, the other needles are either filled with the antimicrobial agent, or are connected to a reservoir of the agent, and the same capillary action that pulls the fluid out of the wound forces the agent, which is in liquid form, down the needles and into the wound.

In addition, due to the principle of chemotaxis, any organisms affected by the microbial agent will be driven up the microneedles to the absorbent layer, in order to avoid contact with the antimicrobial agent.

In a preferred embodiment, the antimicrobial agent is in communication with approximately half of the microneedles, with the other half being used to absorb the fluid from the wound.

In order to keep the antimicrobial agent from exiting the microneedles prior to use, a cover layer is placed over the absorbent layer and ends of the microneedles. The cover layer is removed immediately prior to use, which then allows the antimicrobial agent to flow through the microneedles and into the wound.

Any suitable antimicrobial agent can be used in the bandage according to the invention. In one embodiment, the antimicrobial agent is pre-loaded into the microneedles. The antimicrobial agent can be microencapsulated so that it can be released into the wound in a time-release manner, thus providing long term treatment.

The microneedles can be disposed in any suitable pattern on the bandage. In one embodiment, the fraction of microneedles in communication with the antimicrobial agent is disposed homogeneously on one side of the bandage, while the microneedles with no connection to the antimicrobial agent are disposed on an opposite side of the bandage.

In another embodiment, the microneedles in communication with the antimicrobial agent are disposed evenly over the entire surface area of the absorbent layer.

In a preferred embodiment, the absorbent layer is a foam or woven material, such as gauze. Upon contact with fluids from a wound, the gauze absorbs the fluid, and further acts to pull the fluid and any infectious microorganisms away from the wound.

In order to prevent the absorbent layer from sticking to a wound, there can be a non-stick layer connected to a surface of the absorbent layer. The non-stick layer can be formed of any suitable material such as silicone or other polymer. The non-stick layer is formed to be permeable so that the microneedles can penetrate the layer and fluids from the wound can pass through to the absorbent layer. The non-stick layer can be formed a screen or a perforated sheet.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
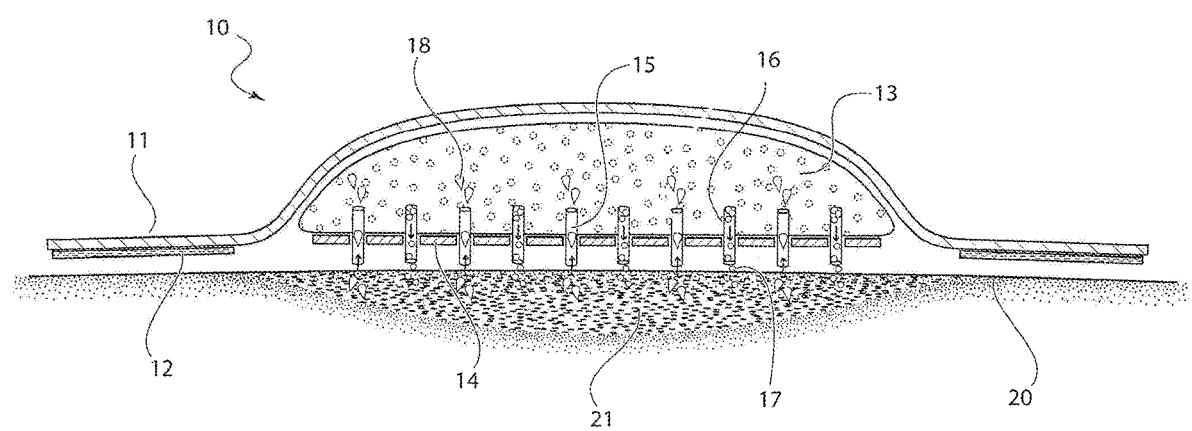
FIG. 1 shows a cross-sectional view of the bandage according to the invention prior to use.

Referring now in detail to the drawings, FIG. 1 shows a cross-sectional view of the bandage 10 according to the invention after application to a patient's skin 20 for covering a wound 21. Bandage 10 comprises a film layer 11, an adhesive layer 12 extending the length of film layer 11, and an absorbent layer 13 disposed centrally along film layer 11, so that end sections 17 of film layer 11 extend beyond absorbent layer 13. A non-stick layer 14 is applied to the bottom of absorbent layer 13 to prevent absorbent layer 13 from sticking to the wound 21. Non-stick layer 14 is water permeable and can be configured as a screen or with perforations to allow fluid to pass through to absorbent layer 13. Non-stick layer 14 can be configured of any suitable material, such as silicone or polypropylene. Film layer 11 can be manufactured from any suitable film material that is commonly used in disposable bandages. Common film materials are extruded polymers, but woven materials could also be used instead of a film.

Embedded within absorbent layer 13 is a microencapsulated antimicrobial agent 17. The antimicrobial agent 17 is configured to be released from microencapsulation upon contact with fluid, so that the agent can mix with the fluid and kill any microoganisms in the fluid. Absorbent layer 13 can be formed of any suitable material, such as foam or gauze.

Antimicrobial agent 17 can be any suitable agent, such as a topical antibiotic (erythromycin, sulfacetamide sodium, bacitracin, neomycin) or antiseptic (sodium hypochlorite, ethanol, iodine, chlorhexidine). By pulling the fluid out of the wound, bandage 10 prevents infection in the wound and speeds healing.

A plurality of microneedles 15, 16, are disposed in the bandage 10, extending between the absorbent layer 13 and the wound 21. Needles 15 act to absorb fluid 18 from wound 21 and store it in absorbent layer 13. Needles 16 are filled with microencapsulated antimicrobial agent 17, which is released through needles 16 and travels into wound 21 to speed healing. The combined action of needles 15, 16 acts to decrease inflammation and infection, while keeping the wound dry. The needles 15, 16, act as conduits both into and out of the wound 21, so that over time, fluid collecting in the wound area is continually suctioned away and treated, thus decreasing healing time and risk of infection. The needles 15 that absorb the fluid from the wound 21 are attached directly to the absorbent material, and capillary action forces the fluid 18 from the wound 21 up the needles 15, where it is absorbed by the absorbent layer 13. At the same time, the capillary action forces the antimicrobial agent 17, which is in liquid form, down the needles 16 and into the wound.

In addition, due to the principle of chemotaxis, any organisms affected by the antimicrobial agent 17 will be driven up the microneedles 15 to the absorbent layer 21, in order to avoid contact with the antimicrobial agent 17.

Figure 2:
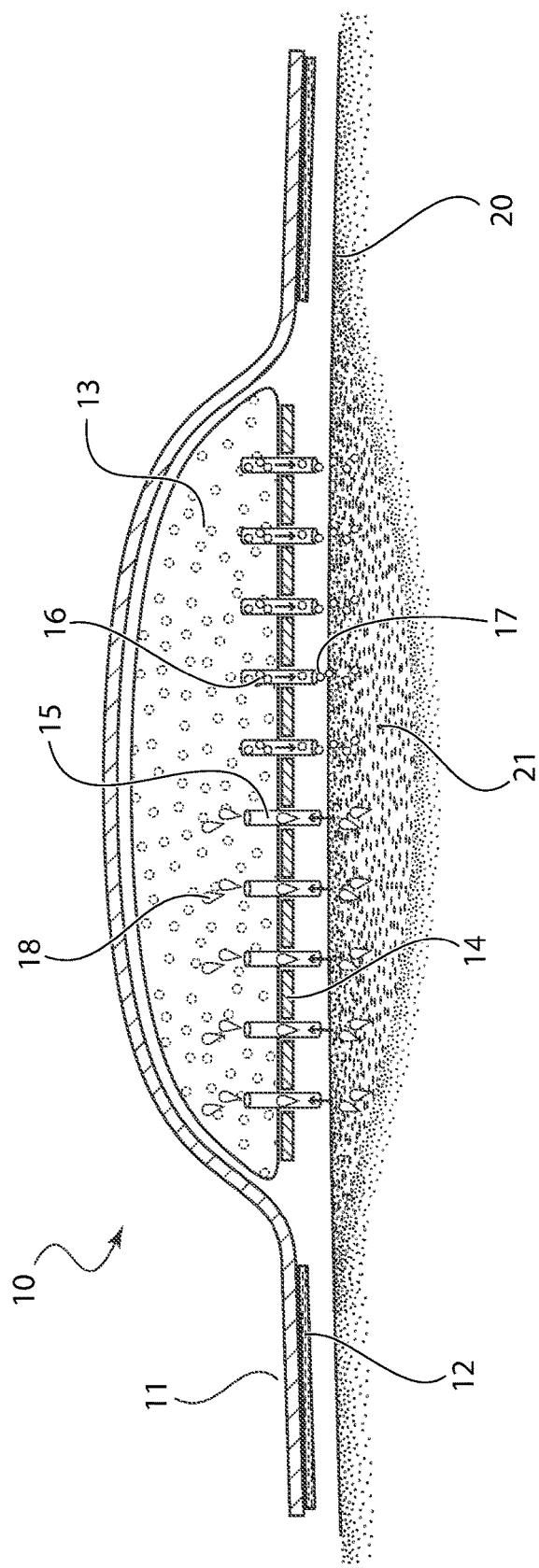
FIG. 2 shows another embodiment of the bandage.

As shown in FIG. 1, the needles 15, 16 are disposed uniformly throughout the bandage, so that the suction of wound fluid and the dispensing of the antimicrobial agent takes place evenly throughout the area. However, other arrangements could also be used, such as the one in FIG. 2, where all needles 15 are on one side of the bandage 10, and all needles 16 are on the other side, so that suction of the fluid 18 occurs on one side and dispensing of the antimicrobial agent 17 occurs on the other side.

Figure 3:
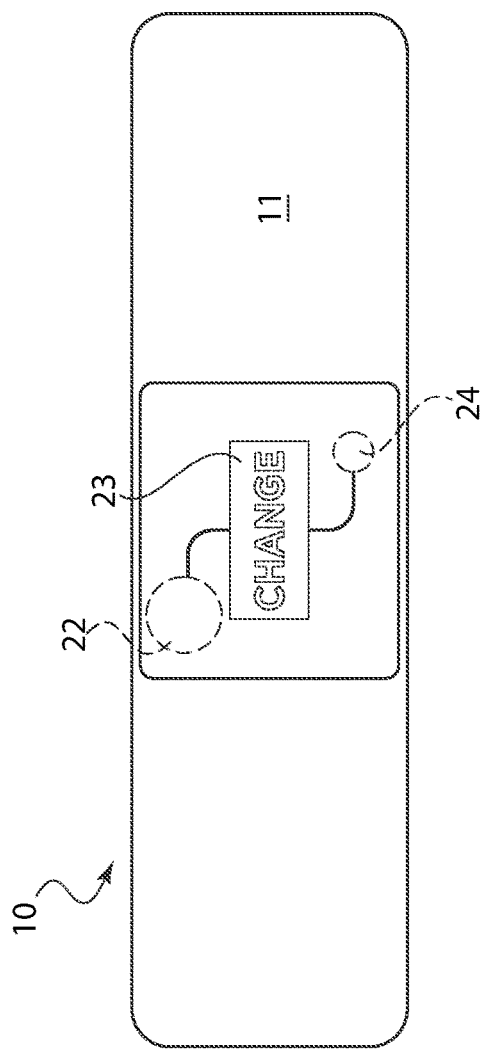
FIG. 3 shows a top view of the bandage.

As shown in FIG. 3, there can be a layer of electronic ink 23 disposed on the film layer 11, a battery 22 connected to the electronic film layer, and a moisture sensor 24 connected to the electronic film layer and the absorbent layer, wherein the electronic film layer 23 displays a message when the moisture sensor 24 senses a predetermined level of moisture in the absorbent layer 13, thus indicating time to change the bandage.

Figure 4:
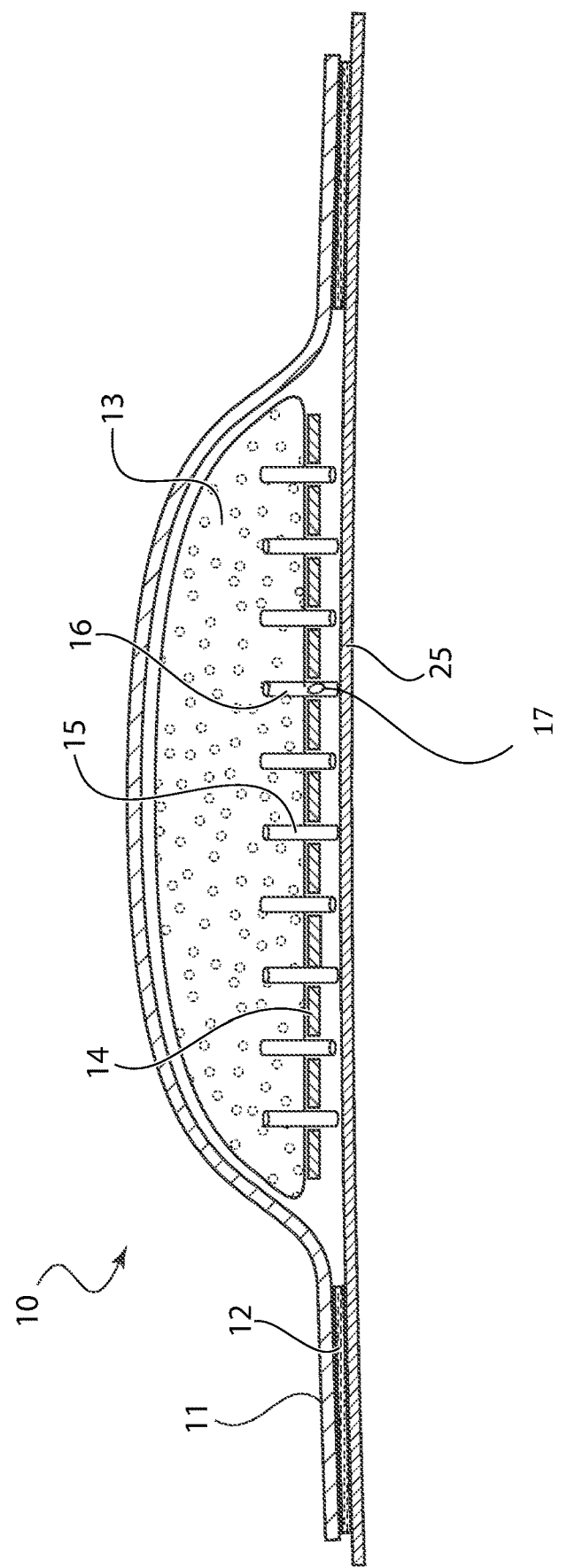
FIG. 4 shows the bandage prior to use.

As shown in FIG. 4, a release layer 25 can be placed on the bottom of the bandage to protect adhesive layer 12 as well as prevent antimicrobial agent 17 from leaking out of needles 16 prior to use.

Accordingly, while only a few embodiments of the present invention have been shown and described, it is obvious that many changes and modifications may be made thereunto without departing from the spirit and scope of the invention.

What is claimed is:
1. A bandage comprising:
a film layer having a top surface and a bottom surface;
an adhesive applied to the bottom surface; and
an absorbent layer connected to the bottom surface,
a plurality of microneedles disposed within the absorbent layer, each microneedle of said plurality of microneedles having an end that extends through the absorbent layer and is configured to penetrate a wound when the bandage is applied over the wound;
an antimicrobial agent in communication with a fraction of a total quantity of said plurality of microneedles, so that upon application of the bandage to the wound, the antimicrobial agent is transported though said fraction of the total quantity of said plurality of microneedles to the wound,
wherein the remainder of the total quantity of said plurality of microneedles not in communication with the antimicrobial agent are configured to transport fluid from the wound to the absorbent layer.
2. The bandage according to claim 1, wherein the fraction of the total quantity of the plurality of microneedles comprises half of the plurality of microneedles.
3. The bandage according to claim 1, further comprising a release layer extending over the absorbent layer and said ends of the plurality of microneedles, said release layer preventing the antimicrobial agent from exiting the fraction of the total quantity of the plurality of microneedles, and wherein removal of the release layer allows the antimicrobial agent to flow through the fraction of the total quantity of the plurality of microneedles and into the wound.
4. The bandage according to claim 3, wherein the antimicrobial agent is disposed inside the fraction of the total quantity of the plurality of microneedles prior to removal of the release layer.
5. The bandage according to claim 1, wherein the fraction of the total quantity of the plurality of microneedles in communication with the antimicrobial agent is disposed homogeneously on one side of the bandage, while the remainder of the total quantity of the plurality of microneedles with no connection to the antimicrobial agent are disposed on an opposite side of the bandage.
6. The bandage according to claim 1, wherein the fraction of the total quantity of said plurality of microneedles in communication with the antimicrobial agent are disposed evenly over the entire surface area of the absorbent layer.

7. The bandage according to claim 1, wherein the film layer extends in at least two directions beyond edges of the absorbent layer.

8. The bandage according to claim 1, wherein the absorbent layer is a woven fabric or foam.

9. The bandage according to claim 1, further comprising a non-stick layer connected to a surface of the absorbent layer.

10. The bandage according to claim 1, wherein the antimicrobial agent is microencapsulated.

11. The bandage according to claim 10, wherein the microencapsulation is configured so that the antimicrobial agent is released in a time-delayed manner.

12. The bandage according to claim 1, further comprising a layer of electronic ink disposed on the film layer, a battery connected to the electronic ink layer, and a moisture sensor connected to the electronic ink layer and the absorbent layer, wherein the electronic ink layer displays a message when the moisture sensor senses a predetermined level of moisture in the absorbent layer.

\* \* \* \* \*